US009999400B2

(12) United States Patent
Behrooz et al.

(10) Patent No.: US 9,999,400 B2
(45) Date of Patent: Jun. 19, 2018

(54) SYSTEMS AND METHODS FOR AUTOMATED SEGMENTATION OF INDIVIDUAL SKELETAL BONES IN 3D ANATOMICAL IMAGES

(71) Applicants: PerkinElmer Health Sciences, Inc., Waltham, MA (US); PerkinElmer Cellular Technologies Germany GmbH, Tallinn (EE)

(72) Inventors: Ali Behrooz, Waltham, MA (US); Peet Kask, Harjumaa (EE)

(73) Assignee: PerkinElmer Health Services, Inc., Waltham, MA (US)

( * ) Notice: Subject to any disclaimer, the term of this patent is extended or adjusted under 35 U.S.C. 154(b) by 128 days.

(21) Appl. No.: 14/812,483

(22) Filed: Jul. 29, 2015

(65) Prior Publication Data
US 2017/0032518 A1    Feb. 2, 2017

(51) Int. Cl.
*G06K 9/00* (2006.01)
*A61B 6/00* (2006.01)
(Continued)

(52) U.S. Cl.
CPC ............. *A61B 6/505* (2013.01); *A61B 6/508* (2013.01); *G06K 9/4604* (2013.01); *G06K 9/52* (2013.01);
(Continued)

(58) Field of Classification Search
CPC G06T 7/187; G06T 7/62; G06T 15/00; G06T 15/08; G06T 2207/30008;
(Continued)

(56) References Cited

U.S. PATENT DOCUMENTS 6,625,303 B1 * 9/2003 Young .................... G06T 7/70
382/132
7,539,332 B1   5/2009 Al-Dayeh et al.
(Continued)

FOREIGN PATENT DOCUMENTS

EP        2194505 A1    6/2010
WO    WO-2009/101560 A2    8/2009
(Continued)

OTHER PUBLICATIONS

Laib, A. et al., 3D Micro-Computed Tomography of Trabecular and Cortical Bone Architecture with Application to a Rat Model of Immobilisation Osteoporosis, Medical and Biological Engineering and Computing, 38(3):326-332 (2000).
(Continued)

*Primary Examiner* — Van D Huynh
(74) *Attorney, Agent, or Firm* — Banner & Witcoff, Ltd.

(57) ABSTRACT

Presented herein, in certain embodiments, are approaches for robust bone splitting and segmentation in the context of small animal imaging, for example, microCT imaging. In certain embodiments, a method for calculating and applying single and hybrid second-derivative splitting filters to gray-scale images and binary bone masks is described. These filters can accurately identify the split lines/planes of the bones even for low-resolution data, and hence accurately morphologically disconnect the individual bones. The split bones can then be used as seeds in region growing techniques such as marker-controlled watershed segmentation. With this approach, the bones can be segmented with much higher robustness and accuracy compared to prior art methods.

26 Claims, 13 Drawing Sheets

(51) Int. Cl.
| | |
|---|---|
| *G06K 9/52* | (2006.01) |
| *G06K 9/46* | (2006.01) |
| *G06T 15/08* | (2011.01) |
| *G06T 15/00* | (2011.01) |
| *G06T 7/11* | (2017.01) |
| *G06T 7/187* | (2017.01) |
| *G06T 7/62* | (2017.01) |
| *A61B 6/03* | (2006.01) |

(52) U.S. Cl.
CPC ............... *G06T 7/11* (2017.01); *G06T 7/187* (2017.01); *G06T 7/62* (2017.01); *G06T 15/00* (2013.01); *G06T 15/08* (2013.01); *A61B 6/032* (2013.01); *G06K 2009/4666* (2013.01); *G06T 2200/04* (2013.01); *G06T 2207/30008* (2013.01)

(58) Field of Classification Search
CPC ............ G06T 7/11; G06T 2207/10081; G06K 9/4604; A61B 6/505; A61B 6/032
USPC ......................................................... 382/128
See application file for complete search history.

(56) References Cited

U.S. PATENT DOCUMENTS

| | | | |
|---|---|---|---|
| 8,306,305 B2* | 11/2012 | Porat ....................... | G06T 7/187 382/128 |
| 9,192,348 B2 | 11/2015 | Ollilainen et al. | |
| 2005/0163358 A1* | 7/2005 | Moeller ................. | G06K 9/342 382/128 |
| 2008/0107318 A1 | 5/2008 | Kiraly | |
| 2010/0128954 A1* | 5/2010 | Ostrovsky-Berman ... | G06T 7/11 382/131 |
| 2012/0143037 A1* | 6/2012 | Najarian ................ | A61B 6/032 600/407 |
| 2016/0038124 A1 | 2/2016 | Tsujita | |

FOREIGN PATENT DOCUMENTS

| | | |
|---|---|---|
| WO | WO-2014/050601 A1 | 4/2014 |
| WO | WO-2017/019059 A1 | 2/2017 |

OTHER PUBLICATIONS

Lee, T.C. et al., Building Skeleton Models Via 3-D Medial Surfaces/Axis Thinning Algorithms, CVGIP: Graphical Models and Image Processing, Academic Press, 56(6):462-478 (1994).
Written Opinion, PCT/US2015/042631, dated Apr. 21, 2016, 7 pages.
Fiebich, M. et al., Automatic Bone Segmentation Technique for CT Angiographic Studies, Journal of Computer Assisted Tomography, 23(1):155-161 (1999).
Frangi, A. F. et al., Mutliscale vessel enhancement filtering, Medical Image Computing and Computer-Assisted Intervention, Lecture Notes in Computer Science, 1496:130-137 (1998).
Krčah, M. et al., Fully Automatic and Fast Segmentation of the Femur Bone From 3D-CT Images With No Shape Prior, IEEE, pp. 2087-2090, ISBI2011.
Lemke, H. et al., CAR '97, Computer Assisted Radiology and Surgery, Elsevier, 209-214 (1997).
Meyer, F. and Beucher, S., Morphological Segmentation, Journal of Visual Communication and Image Representation, 1(1):21-46 (1990).
Ballard, Dana H., Model-Directed Detection of Ribs in Chest Radiographs, Computer Science Department, University of Rochester, (1978) 24 pages.
De Bruijne, M. and Nielsen, Multi-object Segmentation Using Shape Particles, IPMI, LNCS 3565:762-773 (2005).
International Search Report, PCT/US2015/042631, dated Apr. 21, 2016, 4 pages.
Khmelinskii, A. et al., Atlas-based organ & bone approximation for ex-vivo ¼ MRI mouse data: A pilot study, IEEE ISBI, 1197-1200 (2010).
Klinder, T. et al., Automated Model-Based Rib Cage Segmentation and Labeling in CT Images, MICCA, Part II, LNCS 4792:195-202 (2007).
Lee, J. and Reeves, A. P., Segmentation of Individual Ribs from Low-dose Chest CT, Medical Imaging, 7624:J1-J8 (2010).
Maier, F. et al., Automatic Liver Segmentation Using the Random Walker Algorithm, Universität Karlsruhe (TH), Siemens Medical Solutions, Forchheim, Friedrich-Alexander University, Erlangen-Nuremberg, RWTH Aachen University, 6 pages (2008).
Staal, J. et al, Automatic rib segmentation and labeling in computed tomography scans using a general framework for detection, recognition and segmentation of objects in volumetric data, Medical Image Analysis 11:35-46 (2007).
Staal, J. et al., Automatic Rib Segmentation in CT Data, CVAMIA-MMBIA, LNCS 3117:193-204 (2004).
Sun, S. et al., Automated 3-D Segmentation of Lungs With Lung Cancer in CT Data Using a Novel Robust Active Shape Model Approach, IEEE Transactions on Medical Imaging, 31(2):449-460 (2012).
Wang, H. et al., Estimation of Mouse Organ OLocations Through Registration of a Statistical Mouse Atlas With Micro-CT Images, IEEE Transactions on Medical Imaging, 31(1):88-102 (2012).
Wildeman, M. H. et al., 2D/3D Registration of Micro-CT Data to Multi-View Photographs Based on a 3D Distance Map, Biomedical Imaging, IEEE International Symposium ON, 987-990 (2009).
Wlodarczyk, J. et al., Segmentation of bones in magentic resonance images of the wrist, International Journal of Computer Assisted Radiology and Surgery, 10(4):419-431 (2014).
Wu, D. et al, A Learning Based Deformable Template Matching Method for Automatic Rib Centerline Extraction and Labeling in CT Images, IEEE, 980-987 (2012).
Yin, Y. et al., Hierarchical Decision Framework with Priori Shape Models for Knee Joint Cartilage Segmentation—MICCAI Grand Challenge, Depts. of Electrical & Computer Engineering and Orthopaedics & Rehabilitation, University of Iowa, pp. 241-250 (2010).
Li, Q. et al., Selective enhancement filters for nodules, vessels, and airway walls in two- and three-dimensional CT scans, Med. Phys. 30(8):2040-2051 (2003).
Sato, Y. et al., 3D Multi-Scale Line Filter for Segmentation and Visualizaiton of Curvilinear Structures in Medical Images, Medical Image Analysis 2(2):143-168 (1998).
Analyzedirect, Analyze 12.0 Bone Microarchitecture Analysis Manual, AnalyzeDirect, Inc. and BIR, Mayo Clinic, 56 pages, 1999-2014.
Computer Vision Demonstration Website, Electronics and Computer Science University of Southampton, Standard and Hysteresis Thresholding, 2 pages (2005) [retrieved May 3, 2017—<http://users.ecs.saoton.ac.uk/msn/book/new_demo/thresholding/>].
Eddins, Steve, The Watershed Transform: Strategies for Image Segmentation, MathWorks, 8 pages (2002) [retrieved May 3, 2017—<https://www.mathworks.com/company/newsletters/articles/the-watershed-transform-strategies-for-image-segmentation.html>].
Otsu, Nobuyuki, A Threshold Selection Method from Gray-Level Histograms, IEE Transactions on Systems, Man and Cybernetics, SMC-9(1):62-66 (1979).
Smolka, Jakub, Watershed based region growing algorithm, Annales UMCS Informatica AI, 3:169-178 (2005).
Waarsing, J. H. et al., An Improved Segmentation Method for in Vivo μCT Imaging, Journal of Bone and Mineral Research, 19:1640-1650 (2004).
Wikipedia, Canny edge detector, 9 pages. (2017) [retrieved May 3, 2017—<http://en.wikipedia.org/wiki/Canny_edge_detector>].

* cited by examiner

SYSTEMS AND METHODS FOR AUTOMATED SEGMENTATION OF INDIVIDUAL SKELETAL BONES IN 3D ANATOMICAL IMAGES

TECHNICAL FIELD

This invention relates generally to methods and systems of image analysis. More particularly, in certain embodiments, the invention relates to automatic bone splitting and segmentation from an anatomical image of a small subject (e.g., small animal, small mammal), e.g., captured with a computed tomography (CT) scanner.

BACKGROUND

There is a wide array of technologies directed to in vivo imaging of mammals—for example, bioluminescence, fluorescence, tomography, and multimodal imaging technologies. In vivo imaging of small mammals is performed by a large community of investigators in various fields, e.g., oncology, infectious disease, and drug discovery.

In vivo micro computed tomography (hereafter, "microCT") imaging, is an x-ray-based technology that can image tissues, organs, and non-organic structures with high resolution, although higher-throughput imaging may make beneficial use of lower resolution microCT imaging to speed image acquisition and/or processing while maintaining acceptable accuracy and image detail. MicroCT has evolved quickly, requiring low dose scanning and fast imaging protocols to facilitate multi-modal applications and enable longitudinal experimental models. In vivo imaging often involves the use of reagents, such as fluorescent probes, for non-invasive spatiotemporal visualization of biological phenomena inside a live animal. Multi-modal imaging involves the fusion of images obtained in different ways, for example, by combining FMT, PET, MRI, CT, and/or SPECT imaging data.

Image analysis applications and/or imaging systems generally allow for visualization, analysis, processing, segmentation, registration and measurement of biomedical images. These applications and systems also provide volume rendering tools (e.g., volumetric compositing, depth shading, gradient shading, maximum intensity projection, summed voxel projection, signal projection); manipulation functions (e.g., to define areas of structures of interest, delete unwanted objects, edit images and object maps); and measurement functions (e.g., for calculation of number of surface voxels, number of exposed faces, planar area of a region, and estimated surface area or volume of a region).

Conventional object segmentation algorithms typically rely on morphological approaches to perform bone splitting. In these approaches, watershed transformation is typically applied to the gray-scale image data or the distance transform of the binary object mask. The watershed transform separates the binary mask into labeled regions which represent the individual objects that make up the binary mask (as discussed, for example, in F. Meyer, S. Beucher, J. Vis. Comm. Im. Rep. 1(1), 1990 21-46). Using this approach, the binary bone mask from FIG. 1 can be separated and labeled as depicted in FIG. 2.

As evident in FIG. 2, this conventional segmentation approach suffers from limitations and drawbacks which result in under-segmentation, over-segmentation, and most importantly, incorrect placement of the split lines/planes. The latter occurs mainly because the combination of distance and watershed transforms place the split lines/planes on the thinnest connectors between the objects. However, the thinnest connectors may or may not coincide with the bone joints. This issue can be seen in the splitting of the femur from the pelvis in the results shown in FIG. 2.

While some existing morphological segmentation techniques may sometimes provide adequate accuracy in high-resolution images of larger mammals (e.g., humans), where the spacing between the objects is larger than the voxel resolution, their performance does not provide adequate accuracy needed for further image processing when dealing with low-resolution data such as the dataset shown in FIG. 1, e.g., for imaging of small animals (e.g., mice, rats, voles, rabbits, and similarly-sized animals). Micro-CT images typically have voxel sizes of about a few microns to a few hundred microns (e.g., between 4.5 microns to 200 microns). In lower resolutions (e.g., corresponding to voxel sizes of 40 microns or higher), partial volume effects can cause two separate objects to get morphologically connected in the binary mask, which can, for example cause significant loss in segmentation accuracy, as shown in FIG. 2. In some embodiments, the image of the subject (e.g., a small mammal subject, e.g., a mouse) has a resolution such that each voxel of the image corresponds to a volume at least 40 microns in each dimension.

While a variety of techniques have been used for splitting and segmentation of large bones in medical (human) CT imaging (e.g., as described by U.S. Pat. No. 8,306,305 B2 by Porat, et al.), there remains a need for robust methods for bone splitting and segmentation for small animal micro-CT imaging. For example, Porat et al. note in U.S. Pat. No. 8,306,305 B2 that the morphological operations described therein may not be appropriate if the method is intended to be used for the skull, since the operations would cause the entire brain to be included in the bone component. Porat et al. further describe that thin parts of the vertebrae may be less than one voxel thick, and the average density of the voxels that contain them may be less than their actual density and that these bones may not be found in their entirety.

A significant difference between the bone splitting and segmentation in large and small animals is that the spatial resolution offered by micro-CT is not always sufficiently higher than the thickness or dimensions of the bones in small animals, such as laboratory mice. This can pose further challenges on bone segmentation considering partial volume effects. Thus, there is a need for improved and accurate methods for automated object segmentation especially in cases such as small animal micro-CT data where high resolution images are not always available, or are too time-consuming or computationally complex to obtain.

SUMMARY OF THE INVENTION

Presented herein, in certain embodiments, are approaches for robust bone splitting and segmentation in the context of small animal imaging. In some embodiments, the segmentation techniques presented herein are useful in anatomical imaging platforms, including micro-CT. In certain embodiments, a method for calculating and applying single and hybrid second-derivative splitting filters to gray-scale images and binary bone masks prior to the watershed segmentation is described. These filters can accurately identify the split lines/planes of the bones even for low-resolution data, and hence accurately disconnect the individual bones. The split bones can then be used as seeds for marker-controlled watershed segmentation. With this approach, the bones can be segmented with much higher robustness and accuracy compared to prior art methods. This improved performance stems from the ability of the splitting filters to accurately locate the separation points/planes of the bones using second-derivative functions.

Automated segmentation of skeletal bones, detected from gray-scale anatomical images via thresholding or similar methods, can allow for bone visualization, morphometric and statistical analyses, and shape, feature, and disease studies. For example, local thresholding techniques can be used to detect the skeletal bones in a micro-CT volume as shown in FIG. 1. The end goal is to segment each bone as an individual object; therefore, it is desirable to automatically split the binary mask shown in FIG. 1 into a segmentation map of differentiated individual bones. Accurate, automated anatomical characterization of specific bones or groups of bones can then be made from the segmentation map of differentiated bones for classification, diagnosis, or other research purposes.

The technique can also be used for automated segmentation of other network-like objects or materials depicted in images. For example, the techniques described herein can be used for differentiating discrete mineral types depicted in a three-dimensional geological image for mineral mapping or for oil and gas development/exploration.

One aspect described herein is directed to a method of performing image segmentation to automatically differentiate individual bones in an image of a skeleton or partial skeleton of a subject, the method including receiving, by a processor of a computing device, an image (e.g., a two-dimensional image or a three-dimensional image, e.g., a three-dimensional image comprising voxels, e.g., a gray-scale image) (e.g., an in vivo image, an ex vivo image, or an in situ image) of a subject (e.g., a small mammal subject, e.g., a mouse) (e.g., obtained by an in vivo imaging system, e.g., a micro-CT imager); applying, by the processor, one or more second derivative splitting filters to the image to produce a split bone mask for the image; determining, by the processor, a plurality of split binary components of the split bone mask by performing one or more morphological processing operations (e.g., by performing connected component analysis and/or by identifying catchment basins using distance and watershed transforms); optionally, quantifying, by the processor, a volume of each split binary component and eliminating one or more components having unacceptably small volume (e.g., eliminating one or more components having a volume below a predetermined threshold); and performing, by the processor, a region growing operation (e.g., a marker-controlled watershed operation) using the split bone mask components as seeds, thereby producing a segmentation map differentiating individual bones in the image.

In some embodiments, the anatomical image is an in vivo image. In some embodiments, the anatomical image is an ex vivo image. In some embodiments, the anatomical image is an in situ image. In some embodiments, the image is a two-dimensional image or a three-dimensional image. In some embodiments, the image is a three-dimensional image comprising voxels. In some embodiments, the image is a gray-scale image.

In some embodiments, the subject is a small mammal subject. In some embodiments, the subject is a mouse. In some embodiments, the image is obtained by an in vivo imaging system. In some embodiments, the image is obtained by a micro-CT scanner.

In some embodiments, one or more morphological operations includes performing connected component analysis and/or identifying catchment basins using distance and watershed transforms. In some embodiments, eliminating one or more components having unacceptably small volume includes eliminating one or more components having a volume below a predetermined threshold. In some embodiments, the region growing operation includes a marker-controlled watershed operation.

In some embodiments, the one or more second derivative splitting filters includes at least one member selected from the group consisting of a LoG (Laplacian of Gaussian), a HEH (highest Hessian eigenvalue, with preliminary Gaussian filtering), and a LEH (lowest Hessian eigenvalue, with preliminary Gaussian filtering).

In some embodiments, the method includes applying a plurality of second derivative splitting filters to the image of the subject to produce the split bone mask. In some embodiments, the applying step includes for each second derivative splitting filter being applied, producing a filtered image and identifying voxels of the filtered image with intensity higher or lower than a threshold (e.g., a predetermined threshold), thereby yielding a split binary mask identifying voxels in the vicinity of a boundary region between adjacent bones; combining the split binary masks by performing one or more logical operations to return the split bone mask (which is a hybrid of the split binary masks), with voxels near bone boundaries removed.

In some embodiments, the method also includes identifying, by the processor, one or more anatomical measurements (e.g., for diagnostic purposes) using the segmentation map.

In some embodiments, the method includes, following the step of producing the segmentation map, accepting feedback from a user identifying one or more segmented regions of the segmentation map for further refinement or recalculation and then: applying, by the processor, one or more second derivative splitting filters to portions of the image corresponding to the one or more user-identified segmented regions to produce a split bone mask; determining, by the processor, split binary components of the split bone mask; and performing, by the processor, a region growing operation using the split bone mask components as seeds, thereby producing a refined or recalculated segmentation map differentiating individual bones in the image (e.g., thereby providing additional splitting to correct for under-segmentation of the one or more regions identified by the user or thereby providing region merging to correct for over-segmentation of the one or more regions identified by the user, e.g., wherein the further refinement or recalculation steps are performed using different splitter filters and/or different parameters than previously used).

In some embodiments, the image of the subject (e.g., a small mammal subject, e.g., a mouse) has a resolution such that each voxel of the image corresponds to a volume at least 40 microns in each dimension.

In some embodiments, at least one of the one or more second derivative splitting filters is applied using one or more rotational invariants of spatial second partial derivatives of the voxel intensities of the image, wherein the image is a three-dimensional gray-scale image.

Another aspect described herein is directed to a system including a processor and a memory having instructions stored thereon, wherein the instructions, when executed by the processor, cause the processor to: receive an image (e.g., a two-dimensional image or a three-dimensional image, e.g., a three-dimensional image comprising voxels, e.g., a gray-scale image) (e.g., an in vivo image, an ex vivo image, or an in situ image) of a subject (e.g., a small mammal subject, e.g., a mouse) (e.g., obtained by an in vivo imaging system, e.g., a micro-CT imager); apply one or more second derivative splitting filters to the image to produce a split bone mask for the image; determine a plurality of split binary components of the split bone mask by performing one or more morphological processing operations (e.g., by performing connected component analysis and/or by identifying catchment basins using distance and watershed transforms); optionally, quantify a volume of each split binary component and eliminating one or more components having unacceptably small volume (e.g., eliminating one or more components having a volume below a predetermined threshold); and perform a region growing operation (e.g., a marker-controlled watershed operation) using the split bone mask components as seeds, thereby producing a segmentation map differentiating individual bones in the image.

In some embodiments, the one or more second derivative splitting filters includes at least one member selected from the group consisting of a LoG (Laplacian of Gaussian), a HEH (highest Hessian eigenvalue, with preliminary Gaussian filtering), and a LEH (lowest Hessian eigenvalue, with preliminary Gaussian filtering).

In some embodiments, the instructions, when executed by the processor, further cause the processor to apply a plurality of second derivative splitting filters to the image of the subject to produce the split bone mask, the applying step comprising: for each second derivative splitting filter being applied, producing a filtered image and identifying voxels of the filtered image with intensity higher or lower than a threshold (e.g., a predetermined threshold), thereby yielding a split binary mask identifying voxels in the vicinity of a boundary region between adjacent bones; combining the split binary masks by performing one or more logical operations to return the split bone mask (which is a hybrid of the split binary masks), with voxels near bone boundaries removed.

In some embodiments, the instructions, when executed by the processor, further cause the processor to identify one or more anatomical measurements (e.g., for diagnostic purposes) using the segmentation map.

In some embodiments, the instructions, when executed by the processor, further cause the processor to, following the step of producing the segmentation map, accept feedback from a user identifying one or more segmented regions of the segmentation map for further refinement or recalculation and then: apply one or more second derivative splitting filters to portions of the image corresponding to the one or more user-identified segmented regions to produce a split bone mask; determine split binary components of the split bone mask; and perform a region growing operation using the split bone mask components as seeds, thereby producing a refined or recalculated segmentation map differentiating individual bones in the image (e.g., thereby providing additional splitting to correct for under-segmentation of the one or more regions identified by the user or thereby providing region merging to correct for over-segmentation of the one or more regions identified by the user, e.g., wherein the further refinement or recalculation steps are performed using different splitter filters and/or different parameters than previously used).

In some embodiments, the image of the subject (e.g., a small mammal subject, e.g., a mouse) has a resolution such that each voxel of the image corresponds to a volume at least 40 microns in each dimension.

In some embodiments, at least one of the one or more second derivative splitting filters is applied using one or more rotational invariants of spatial second partial derivatives of the voxel intensities of the image, wherein the image is a three-dimensional gray-scale image.

Another aspect described herein is directed to a non-transitory computer readable medium having instructions stored thereon, wherein the instructions, when executed by a processor, cause the processor to: receive an image (e.g., a two-dimensional image or a three-dimensional image, e.g., a three-dimensional image comprising voxels, e.g., a gray-scale image) (e.g., an in vivo image, an ex vivo image, or an in situ image) of a subject (e.g., a small mammal subject, e.g., a mouse) (e.g., obtained by an in vivo imaging system, e.g., a micro-CT imager); apply one or more second derivative splitting filters to the image to produce a split bone mask for the image; determine a plurality of split binary components of the split bone mask by performing one or more morphological processing operations (e.g., by performing connected component analysis and/or by identifying catchment basins using distance and watershed transforms); optionally, quantify a volume of each split binary component and eliminating one or more components having unacceptably small volume (e.g., eliminating one or more components having a volume below a predetermined threshold); and perform a region growing operation (e.g., a marker-controlled watershed operation) using the split bone mask components as seeds, thereby producing a segmentation map differentiating individual bones in the image.

Elements of embodiments described with respect to a given aspect of the invention may be used in various embodiments of another aspect of the invention. For example, it is contemplated that features of the dependent claims referring to one independent claim can be used in apparatus and/or methods of any of the other independent claims.

BRIEF DESCRIPTION OF THE DRAWINGS

The foregoing and other objects, aspects, features, and advantages of the invention will become more apparent and may be better understood by referring to the following description taken in conjunction with the accompanying drawings, in which:

FIG. 3 illustrates that a Laplacian filter enhances the contrast from bone to soft tissue especially in the joints, considering their "concave up" behavior, in the gray-scale image, according to an illustrative embodiment of the present disclosure. The top plot shows the Laplacian of the femur/pelvis joint while the bottom plot depicts the gray-scale data of the femur/pelvis joint.

DETAILED DESCRIPTION

Figure 1:
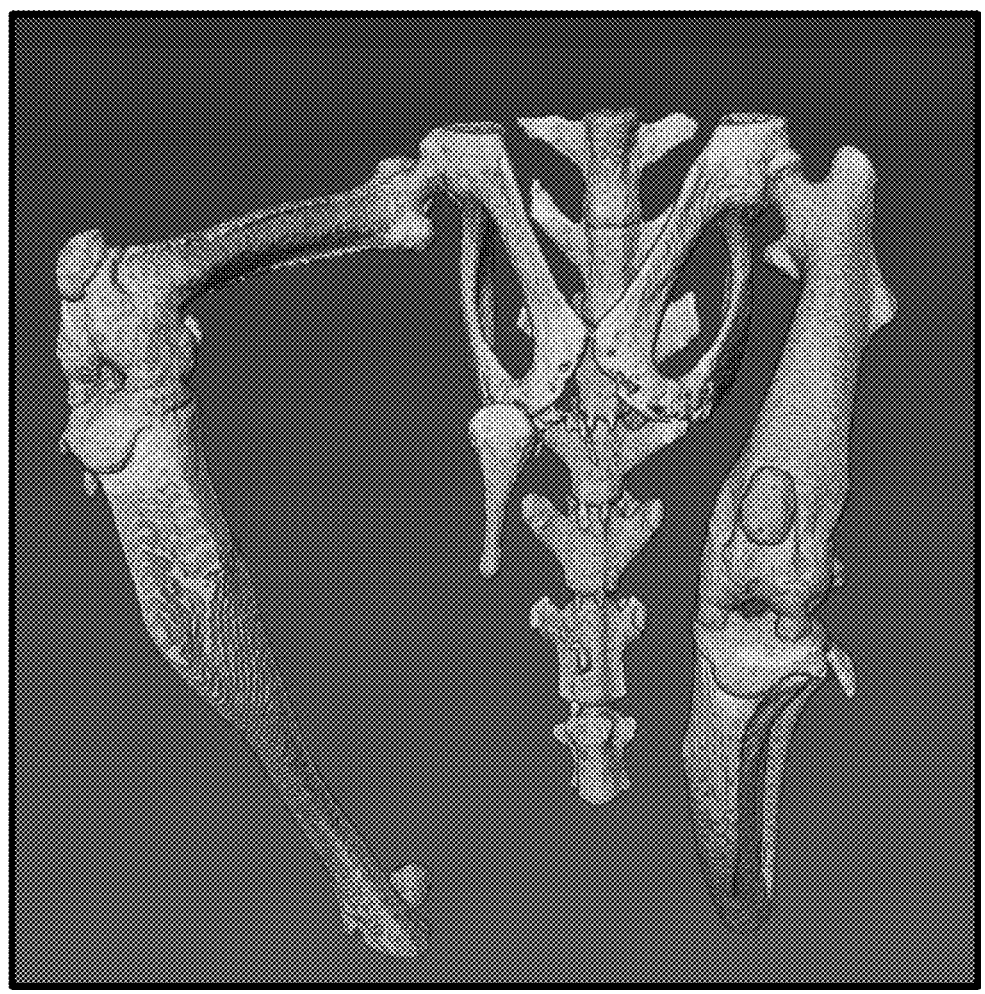
FIG. 1 depicts bones of the lower limbs of a nu/nu mouse imaged by a micro-CT scanner that are detected and visualized using local thresholding techniques. The thresholding process results in a binary mask with unit-valued voxels in the bone area and zero-valued voxels in non-bone areas.

It is contemplated that systems, devices, methods, and processes of the claimed invention encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

As used herein, an "image"—for example, a three-dimensional (hereafter, "3D") image of mammal—includes any visual representation, such as a photo, a video frame, streaming video, as well as any electronic, digital or mathematical analogue of a photo, video frame, or streaming video. Any apparatus described herein, in certain embodiments, includes a display for displaying an image or any other result produced by the processor. Any method described herein, in certain embodiments, includes a step of displaying an image or any other result produced via the method.

As used herein, "3D" or "three-dimensional" with reference to an "image" means conveying information about three dimensions. A 3D image may be rendered as a dataset in three dimensions and/or may be displayed as a set of two-dimensional representations, or as a three-dimensional representation.

As used herein, "bone seed" refers to a set of voxels (e.g., connected set of voxels) which is a part of a bone in a skeleton, and which can be used to find the complete, discrete bone by expanding it (e.g., by repeatedly adding to it neighboring voxels which are likely to be voxels of the same individual bone).

In some embodiments, a bone that can be segmented (e.g., isolated from neighboring bones of a skeleton) is a bone of the legs (e.g., hips, knee caps, femur, etc.), the arms, the hands, the feet, the fingers, the toes, the skull, vertebrae, or collar bones. Some embodiments relate to segmenting a long bone of a mammal (e.g., small mammal, e.g., rat, mice). In some embodiments, a long bone is selected from the following: femora, tibiae, fibulae, humeri, radii, ulnae, metacarpals, metatarsals, phalanges, and clavicles (e.g., of collar bones).

As used herein, a "mask" is a graphical pattern that identifies a 2D or 3D region and is used to control the elimination or retention of portions of an image or other graphical pattern.

As used herein, a "small animal" refers to small mammals that can be imaged with a micro-CT and/or micro-MR imager. In some embodiments, "small animal" refers to mice, rats, voles, rabbits, hamsters, and similarly-sized animals.

As used herein, applying a "second derivative splitting filter" is an image processing operation based on the second derivatives (or approximations thereof) of the intensity of a 3D image, e.g., a gray-scale 3D image, at each of a plurality of voxels. In some embodiments, a splitting filter is derived from Gaussian second derivative filters selected from Laplacian of Gaussian (LoG), highest Hessian eigenvalue with preliminary Gaussian filtering (HEH), and lowest Hessian eigenvalue with preliminary Gaussian filtering (LEH).

Described herein are approaches for robust bone splitting and segmentation in the context of small animal imaging. In certain embodiments, a method for calculating and applying single and hybrid second-derivative splitting filters to gray-scale images and binary bone masks prior to marker-controlled watershed segmentation is described. In some embodiments, the role of a splitting filter is to essentially identify and filter out voxels located in the joint areas between two neighboring bones. Hence, these filters can accurately identify the split lines/planes of the bones even for low-resolution data, and hence morphologically disconnect the individual bones. The split bones can then be used as seeds for marker-controlled watershed segmentation. With this approach, the bones can be segmented with much higher robustness and accuracy compared to prior art methods. This improved performance stems from the ability of the splitting filters to accurately locate the separation points/planes of the bones using second-derivative functions.

In certain embodiments, the splitting filters can be defined based on the second derivatives of a gray-scale 3D image in each voxel. In most embodiments, rotational invariants can be used to make splitting independent of bone orientations. Different rotational invariants of spatial second partial derivatives of the gray-scale 3D image are known, such as Laplacian or eigenvalues of the Hessian matrix or their functions. Laplacian is one which can be calculated without directly solving the eigenvalue problem, and thus offers speed advantages over the others—it is simply the trace of the Hessian matrix. Each rotational invariant can be used in a splitting filter. Furthermore, two or more such filters can be combined in a splitting algorithm to form a hybrid splitting filter. Voxels assigned a high value in a splitting filter can be identified and removed from the binary bone mask. Then, the connected components of the split binary bone mask can be used as seeds (sources) for marker-controlled watershed segmentation.

Figure 3:
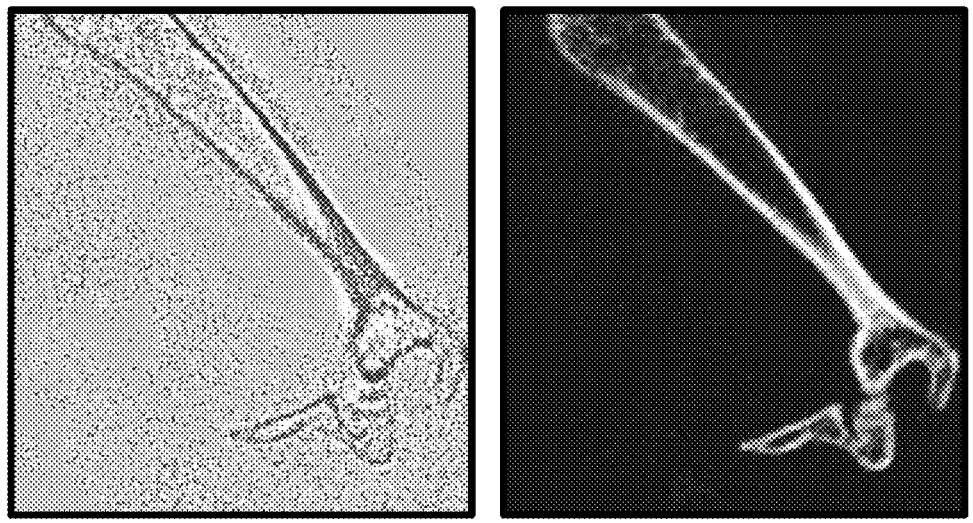
FIG. 3 depicts images of the Laplacian of a femur/pelvis joint of a nu/nu mouse imaged in a micro-CT platform.

The Laplacian, the highest Hessian eigenvalues, and the lowest Hessian eigenvalues are three filters found to be outstanding for splitting, when combined with the other steps of the segmentation methods described herein. The Laplacian describes the extent and sign of concavity (e.g., concave up vs. concave down) of a given voxel in its neighborhood. In the gap between two bones, the intensity is expectedly lower than on bone voxels in a "concave up" fashion; therefore, the Laplacian is positive in the gap voxel. For example, this is demonstrated in FIG. 3 for the femur/pelvis joint. The highest Hessian eigenvalue is also sensitive to the gap between bones since it automatically quantifies intensity in the direction across the valley where the intensity drop is bigger than in any other direction. The lowest Hessian eigenvalue is suited for detecting voxels which belong to a bone rather than a gap between two bones since it automatically quantifies intensity in the direction across the bone.

The Laplacian operator is given by the sum of the second partial derivative of a function (e.g., gray-scale image intensity at a given voxel) with respect to each independent variable, for example, in three dimensions as given by:

$$\Delta f = \frac{\partial^2 f}{\partial x^2} + \frac{\partial^2 f}{\partial y^2} + \frac{\partial^2 f}{\partial z^2},$$

where x, y, and z are standard Cartesian coordinates of the xyz-space.

In certain embodiments, an image is processed using a Hessian matrix. The Hessian is a multiscale second order local structure of an image or a square matrix of second-order partial derivatives of a scalar-valued function (e.g., gray-scale image intensity at a given voxel) that describes the local curvature of the function. For example, applying a Hessian filter to a 3D image comprising voxels (e.g., each voxel having a gray-scale intensity value) may be performed by first applying a set of Gaussian second derivative filters to produce six second derivative images denoted by $L_{xx}$, $L_{yy}$, $L_{zz}$, $L_{xy}$, $L_{xz}$ and $L_{yz}$. Next, the 3×3 Hessian matrix is diagonalized for each voxel. The 3×3 Hessian matrix of second order derivative filtered images is presented as Matrix 1, below:

$$\begin{matrix} L_{xx} & L_{xy} & L_{xz} \\ L_{xy} & L_{yy} & L_{yz} \\ L_{xz} & L_{yz} & L_{zz} \end{matrix} \quad \text{Matrix 1}$$

The diagonalization of the 3×3 Hessian matrix is an eigenproblem. The solution to the eigenproblem includes calculating three eigenvalues which describe the second order derivatives in the directions of three principal components. The eigenvalues can be calculated by solving a cubic equation. In certain embodiments, the directions of principal components are unimportant, and calculation of eigenvectors can be skipped. The result of the diagonalization is the highest, the medium, and the lowest eigenvalues (H, M, L) for each voxel. In other words, in the diagonalization step, three images are calculated from the six images produced by application of the full set of Gaussian second derivative filters. Example embodiments are described herein which identify the highest Hessian eigenvalue (HEH) and/or the lowest Hessian eigenvalue (LEH) for each voxel, and compare one or both of those values (or a hybrid of one or both of those values, and/or the Laplacian) to a threshold.

Calculation of Second-Derivative Splitting Filters

The splitting filters are established using spatial second-derivative operations on the gray-scale image. Examples of such functions include the Laplacian (LAP), the highest, or the lowest eigenvalue of the Hessian (HEH or LEH).

Figure 4:
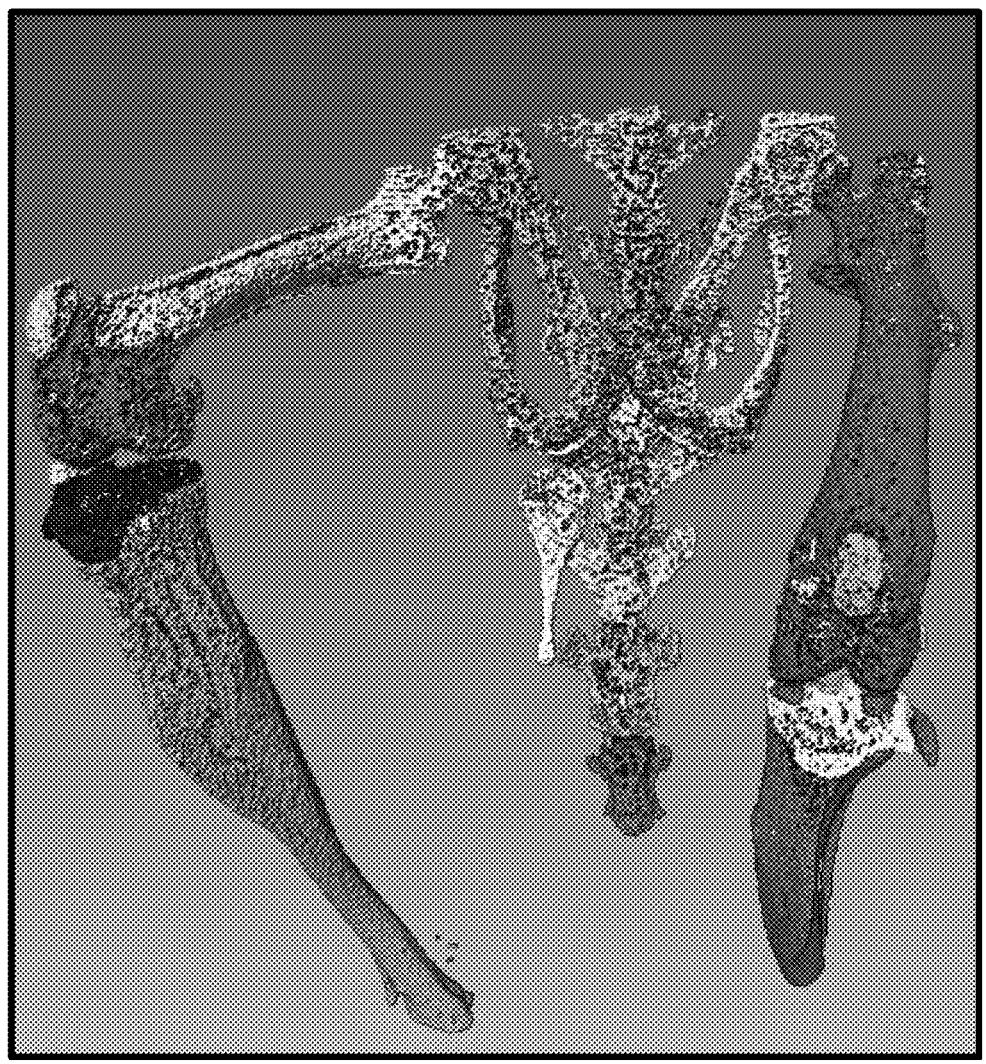
FIG. 4 depicts the connected components of the bone mask from FIG. 1 after Laplacian splitting outlined in FIG. 5, according to an illustrative embodiment of the present disclosure.

The filtering operation consists of identifying voxels in the gray-scale image with high LAP, HEH, or LEH values. These high-valued voxels can be identified using empirical or automated histogram-based thresholding approaches. These voxels essentially include the bone boundaries or boundary points connecting neighboring bones which are of high interest for bone splitting. Once these voxels are identified, they are mapped to the binary bone mask. The mapped binary voxels can then be removed from the bone mask. This morphologically disconnects two closely spaced neighboring bones. The resulting binary mask is the split bone mask. In other embodiments, the split bone mask can be directly calculated by identifying the low-valued voxels in the splitting filter and mapping them to the original bone mask. As an example, the image shown in FIG. 4 depicts the connected components of the binary bone mask from FIG. 1 after LAP-based splitting.

Figure 5:
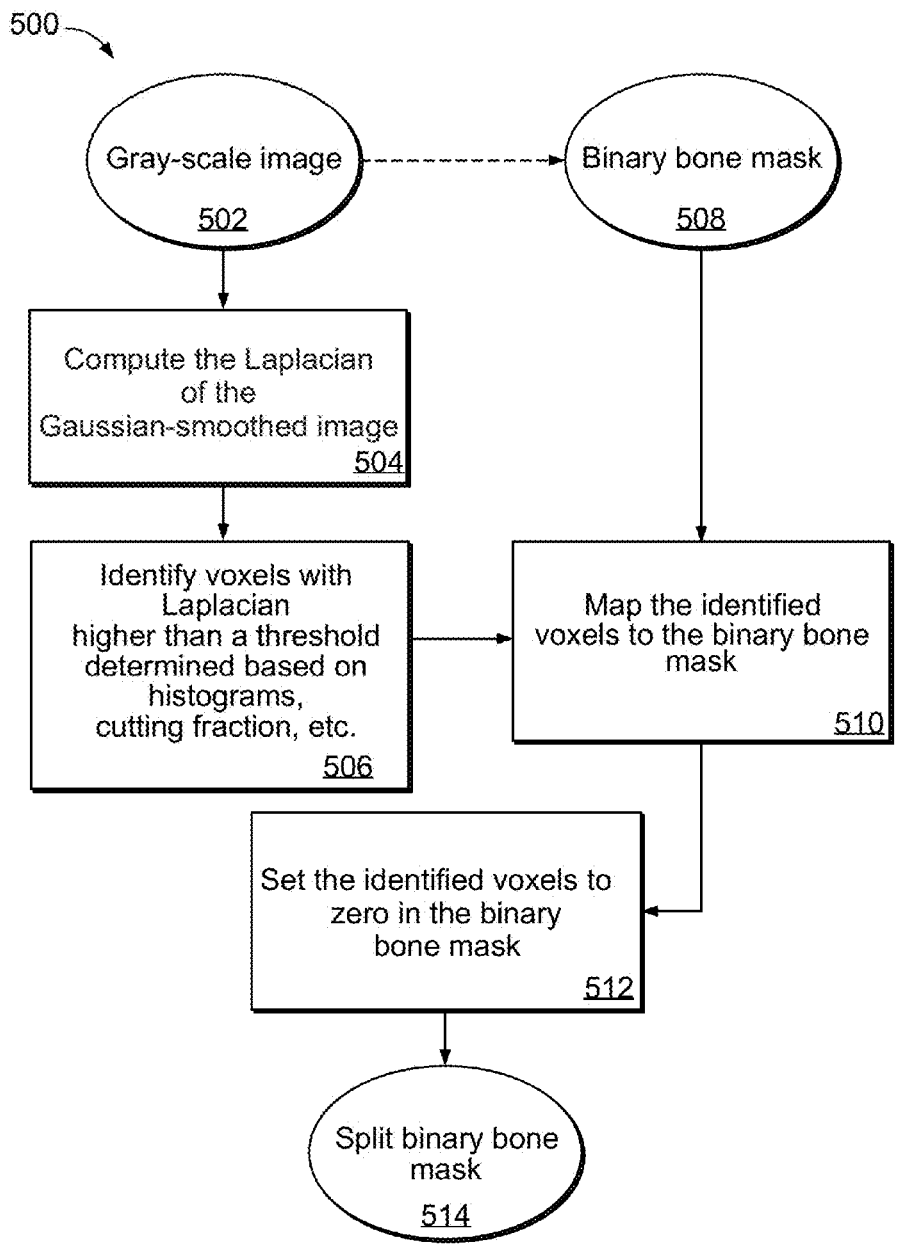
FIG. 5 is a flow-chart showing a calculation and application of Laplacian-based splitting filter to bone data, according to an illustrative embodiment of the present disclosure.

The flow-chart 500 shown in FIG. 5 summarizes the associated workflow for calculating and applying the LAP splitting filter to the gray-scale image. The process begins with obtaining the gray-scale image 502. As shown in FIG. 5, a Laplacian of the gray-scale image (e.g., Gaussian-smoothed image) can be computed in step 504. In some embodiments, the gray-scale image is converted into a binary bone mask in step 508 using thresholding techniques. After the Laplacian of the image (e.g., Gaussian-smoothed image) is computed in step 504, voxels with Laplacian higher than a threshold determined based on histograms, cutting fraction, etc. are identified in step 506. Next, the identified voxels with high-valued Laplacians based on cutting fraction, histograms, etc. are mapped to the binary bone mask in step 510. As shown in FIG. 5, step 510 is carried out after step 508 and step 506. Next, the identified voxels in the binary bone mask are set to zero in step 512 to generate a split binary bone mask in step 514.

While LAP or HEH splitting filters can individually provide significant improvements for bone splitting, they yield highly accurate splitting results when combined. In certain embodiments, LAP filter and the HEH filter can complement each other in bone splitting as the LAP filter succeeds where the HEH filter fails and vice versa. Two or more splitting filters can be combined by performing a voxel-by-voxel "AND" operation between their resulting split binary masks. As an example, the split binary bone mask from the flow-chart in FIG. 5 can be combined with a split binary bone mask from HEH splitting filter to produce a hybrid split binary bone mask, as shown, for example in FIG. 11C. This approach can be used to obtain hybrid filters which combine the benefits of two or more second-derivative splitting filters.

Steps for Preforming Automated Bone Segmentation Using Splitting Filters

Figure 6:
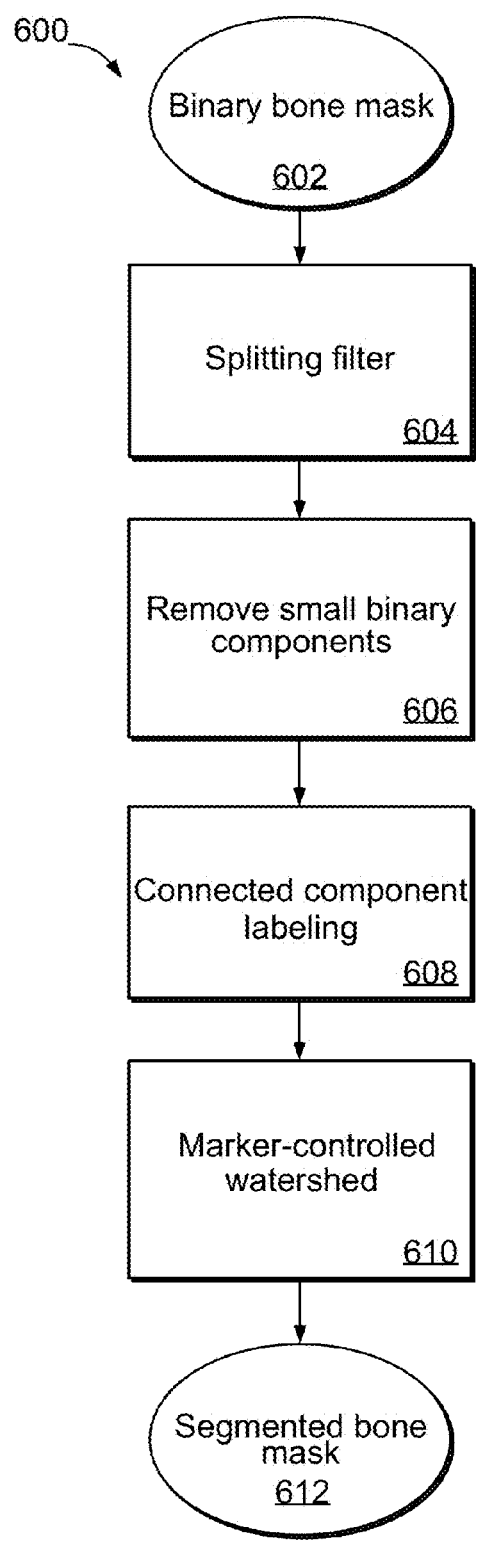
FIG. 6 is a flow chart showing steps associated with performing automated segmentation using splitting filters, according to an illustrative embodiment of the present disclosure.

The splitting-based bone segmentation can be done in four major steps as outlined in the flow-chart 600 in FIG. 6. The segmentation process begins with the binary mask of the bone in step 602. In the first step, the binary mask of the bone undergoes splitting in step 604 as described in the previous section and outlined in the flow-chart 500 of FIG. 5.

Once splitting is performed in step 604, small binary components are removed from the split mask in step 606. As shown in FIG. 4, occasional over-splitting may result in small isolated binary components. However, these components can be easily removed by morphological operations. For example, in some embodiments, these components may be removed by identifying the connected components of the binary split mask and deleting components with a low number of voxels (e.g., below the minimum expected bone size).

In some embodiments, split components of the split bone mask are determined through morphological processing (e.g., connected component analysis or catchment basins from distance and watershed transforms);

After the small binary components are removed from the split mask in step 606 (or after the morphological operations are performed, if needed), in some embodiments, the connected components are labeled in step 608. In other embodiments, split components of the split bone mask are labeled using watershed-based segmentation. After the labeling step 608, the segmented bone mask is obtained in step 610 by applying region growing techniques such as marker-controlled watershed to expand the labeled split components of the split bone mask to fill the entire binary bone mask and produce a labeled bone mask.

It can be noted that the connected components of the split binary masks are only used as seeds for marker-controlled watershed performed in step 610. Thus, removal of small binary components in step 606, or in general, removal of regions or parts of split objects, does not produce artifacts in the final segmentation results, which are obtained in step 612. This is true as long as the connectivity of the major components are not jeopardized.

Figure 7:
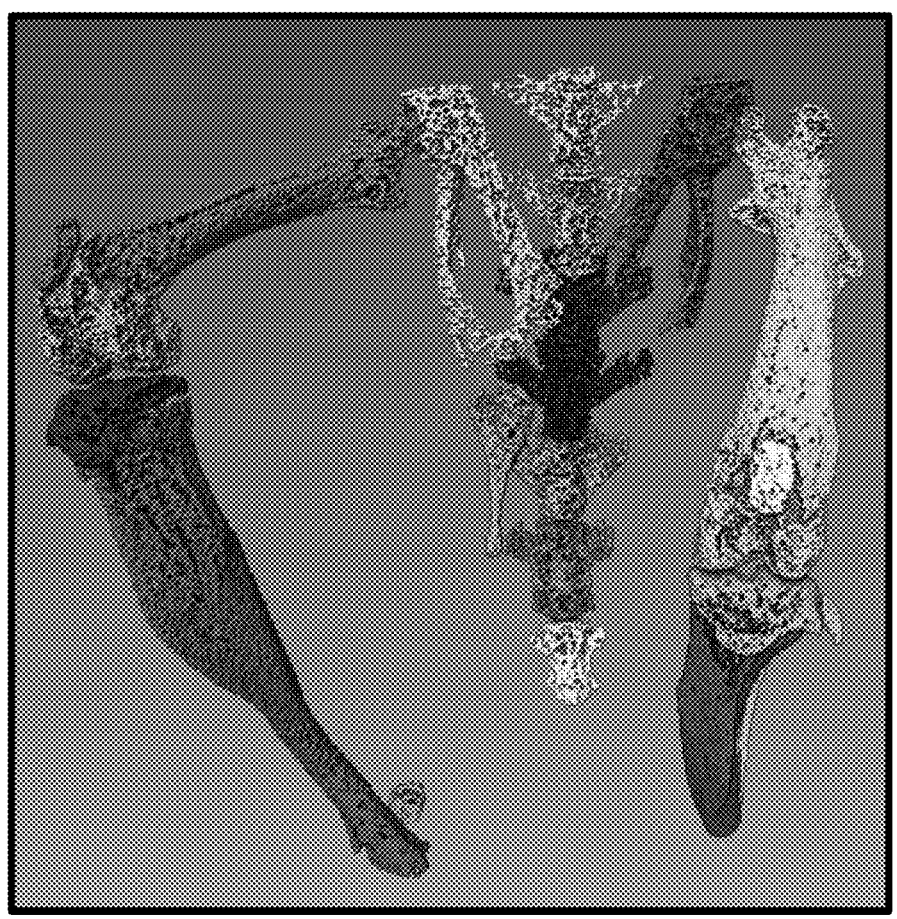
FIG. 7 is an image depicting the production of seeds for marker-controlled watershed produced by removing small binary components of the split binary bone mask created by hybrid LAP-HEH splitting filter, according to an illustrative embodiment of the present disclosure.

In some embodiments of step 608, the connected components of the binary mask can be identified and labeled using 6-order connectivity or higher order connectivity. In some embodiments, the connected components of the binary mask can be identified and labeled through connected component analysis, which is a digital image processing technique based on graph traversal. This step produces the seeds for marker-controlled watershed as shown in FIG. 7. The split mask used for the labeled seeds shown in FIG. 7 was created by applying a hybrid LAP-HEH splitting filter to the gray-scale images of the dataset shown in FIG. 1.

Figure 8:
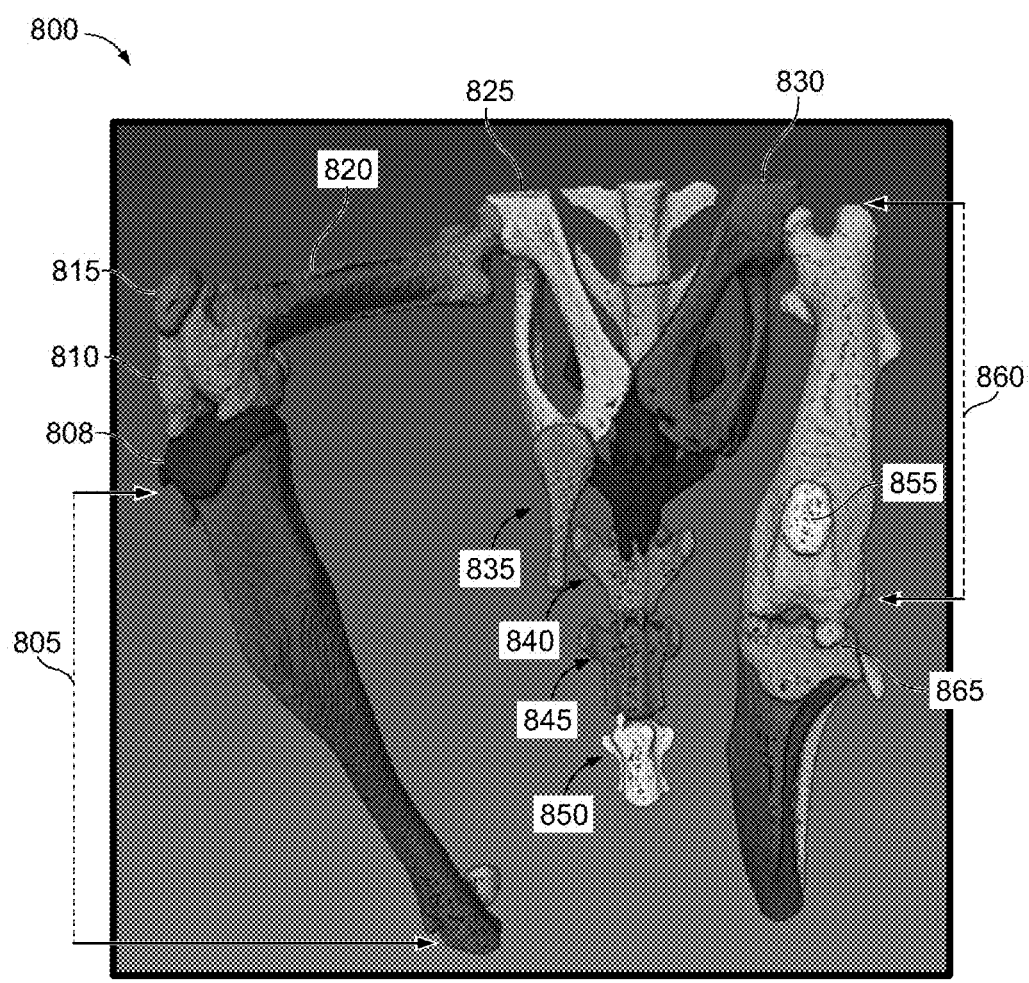
FIG. 8 is an image that depicts a final segmentation result of automated splitting-based segmentation using the seeds from FIG. 7 and a hybrid LAP-HEH splitting filter, according to an illustrative embodiment of the present disclosure.

In some embodiments of step 610, the labeled seeds are used in a marker-controlled watershed segmentation to produce the final segmentation map as shown in FIG. 8.

Figure 2:
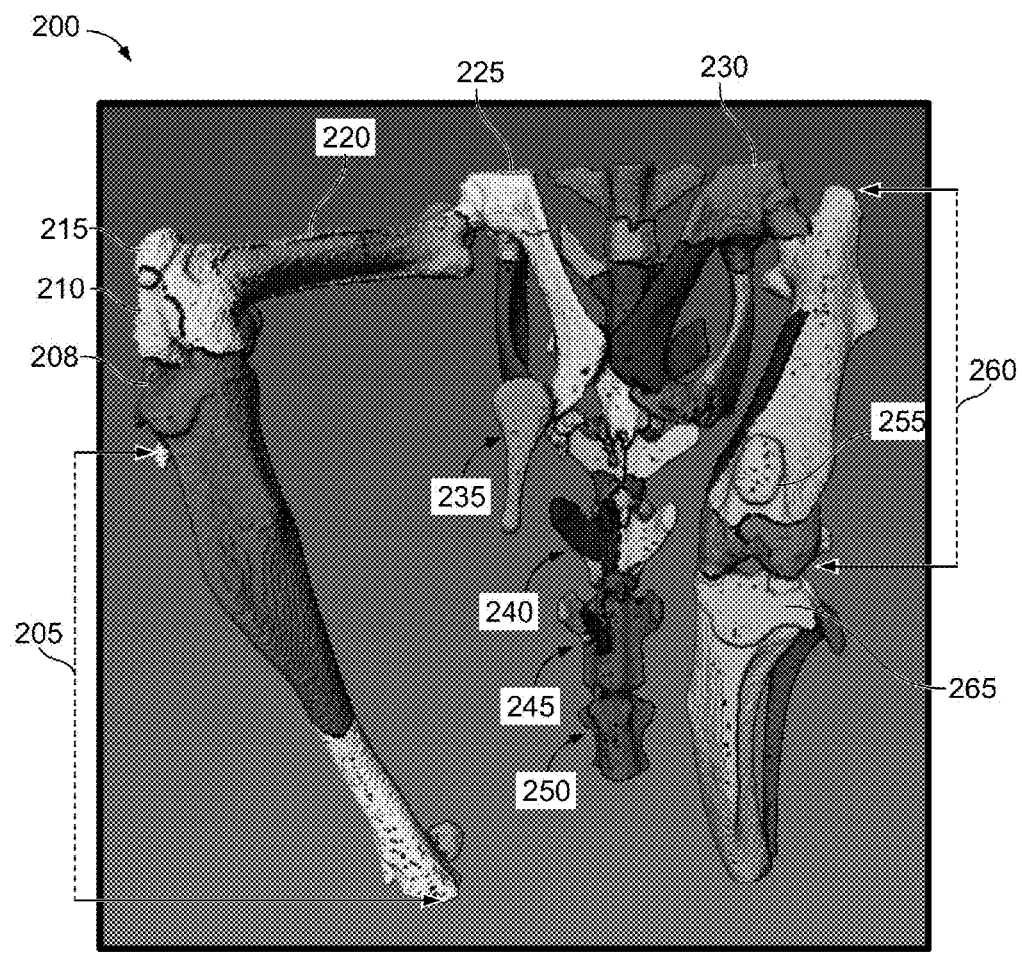
FIG. 2 depicts segmentation of the bones from FIG. 1 using existing distance and watershed transform approach. In addition to over- and under-segmentation issues, this approach cannot locate the split areas accurately as evident in the pelvis-femur splits.

FIG. 8 lacks the limitations and drawbacks seen in FIG. 2 (e.g., under-segmentation, over-segmentation, and incorrect placement of the split lines/planes). For example, FIG. 2 shows skeletal bones 200, which have been inaccurately segmented into bones 205-260 by conventional methods. In contrast, FIG. 8 shows skeletal bones 800, which are accurately segmented into bones 805-860 via the methods described herein. Examples of over-segmentation are seen in FIG. 2, such as in tibia 205. In contrast, as seen in FIG. 8, tibia 805 has been accurately segmented into one bone using the methods described herein. Moreover, hips 225 and 230 have been over-segmented in FIG. 2. In contrast, hips 825 and 830 have been accurately segmented into individual hips in FIG. 8. Examples of under-segmentation, such as in vertebrae 240, 245, and 250, are also seen in FIG. 2. In contrast, vertebrae 840, 845, and 850 have been accurately segmented into vertebrate via the methods described herein. Additional examples of under- and/or over-segmentation are seen in FIG. 2 in the knee caps 215 and 255 and femurs 205 and 260. In contrast, FIG. 8 accurately segments knee cap 815 and 855 and femurs 805 and 860.

In some embodiments, additional correction is needed through user interaction. In such cases, either additional splitting is applied to correct for under-segmentation, or region merging is performed to correct for over-segmentation. In some embodiments, following the step of producing the segmentation map, the method includes accepting feedback from a user identifying one or more segmented regions of the segmentation map for further refinement and recalculation. In some embodiments, following accepting the user feedback, the method includes applying, by the processor, one or more second derivative splitting filters to portions of the image corresponding to the one or more user-identified segmented regions to produce a split bone mask. In some embodiments, following applying the one or more second derivative splitting filters, the method includes determining, by the processor, split binary components of the split bone mask. In some embodiments, following determining the split binary components of the split bone mask, the method includes performing, by the processor, a region growing operation using the split bone mask components as seeds, thereby producing a refined or recalculated segmentation map differentiating individual bones in the image. In some embodiments, producing the refined or recalculated segmentation map includes thereby providing additional splitting to correct for under-segmentation of the one or more regions identified by the user. In some embodiments, producing the refined or recalculated segmentation map includes thereby providing region merging to correct for over-segmentation of the one or more regions identified by the user, e.g., wherein the further refinement or recalculation steps are performed using different splitter filters and/or different parameters than previously used.

Applications

Figure 11A:
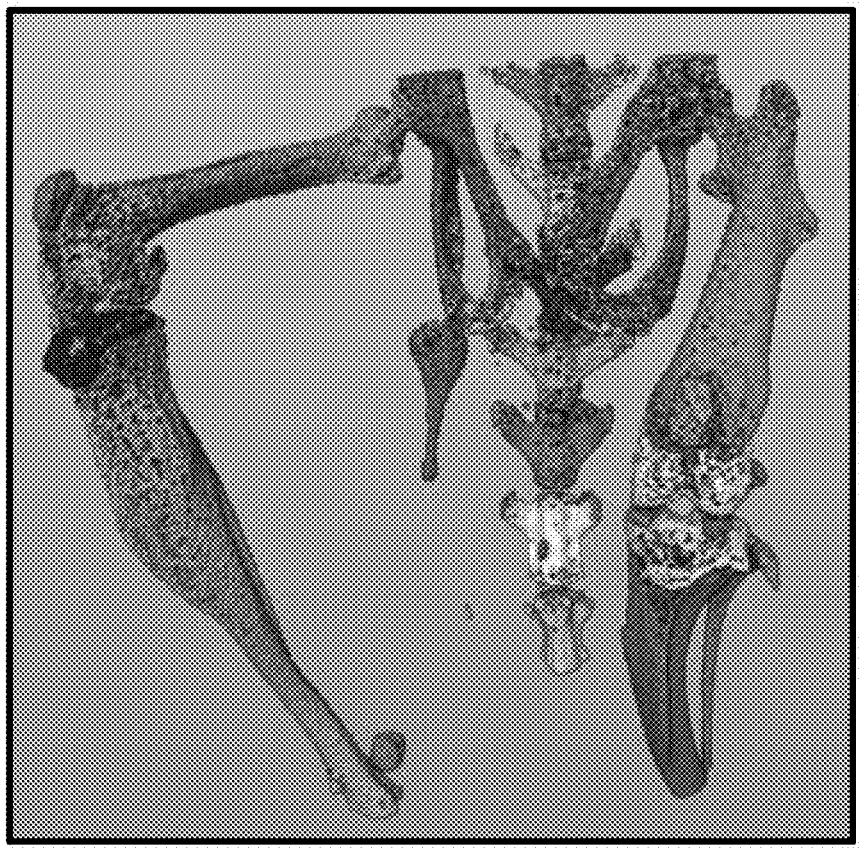
FIG. 11A depicts labeled seeds from LAP split masks, for use in illustrative embodiments of the invention.
Figure 11B:
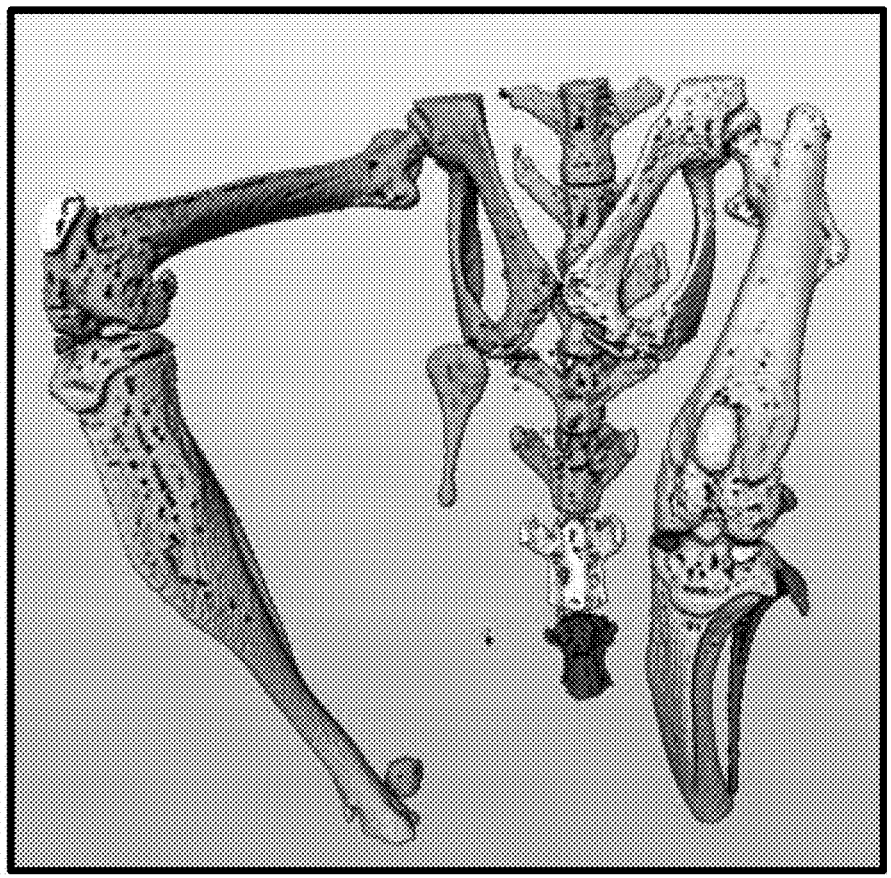
FIG. 11B depicts labeled seeds from HEH split masks, for use in illustrative embodiments of the invention.
Figure 11C:
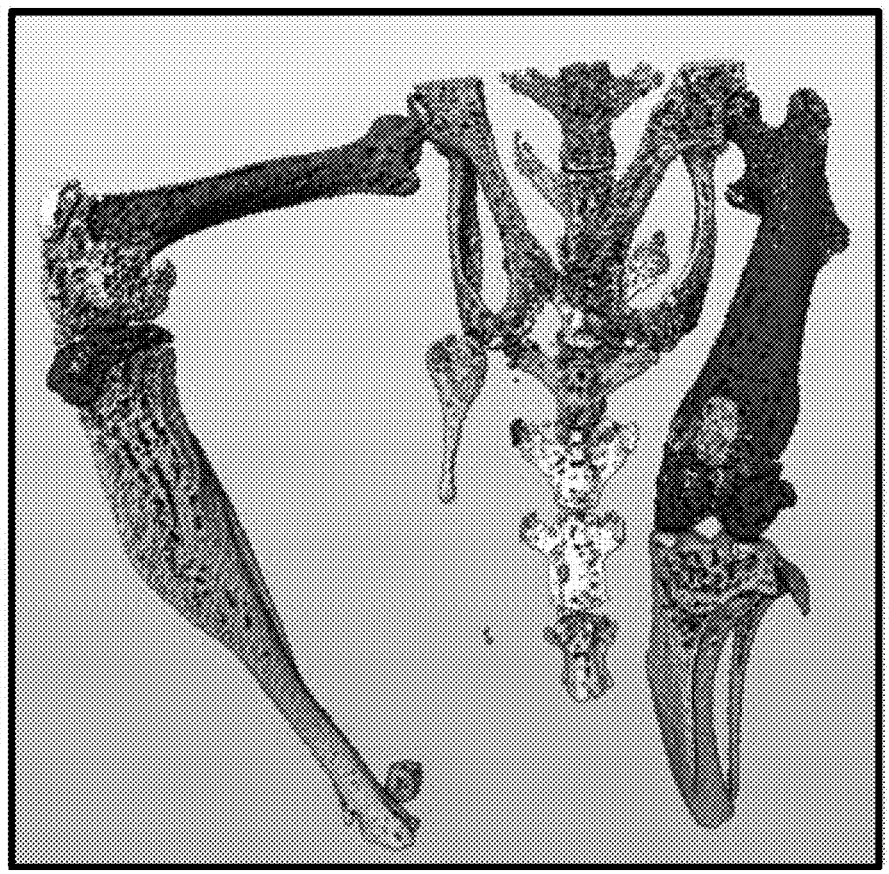
FIG. 11C depicts labeled seeds from hybrid LAP-HEH split masks, for use in illustrative embodiments of the invention.

As discussed above, in certain embodiments, the application for the splitting-based segmentation comprises 3D small animal bone segmentation. Hybrid second-derivative splitting filters, such as LAP-HEH, can separate the binary bone mask into connected components which accurately seed the individual bones as seen in FIGS. 7 and 11C. Considering the level of accuracy and robustness that splitting filters can bring to object segmentation, especially for 3D images, there is a variety of different applications where these filters would be necessary for accurate automated segmentation. Examples include, but are not limited to, 3D organ, fat, rock, or natural mineral/material segmentation. Also, gray-scale images produced from imaging platforms other than micro-CT, such as micro-MR imagers, can be used in splitting-based segmentation.

Hardware

Figure 9:
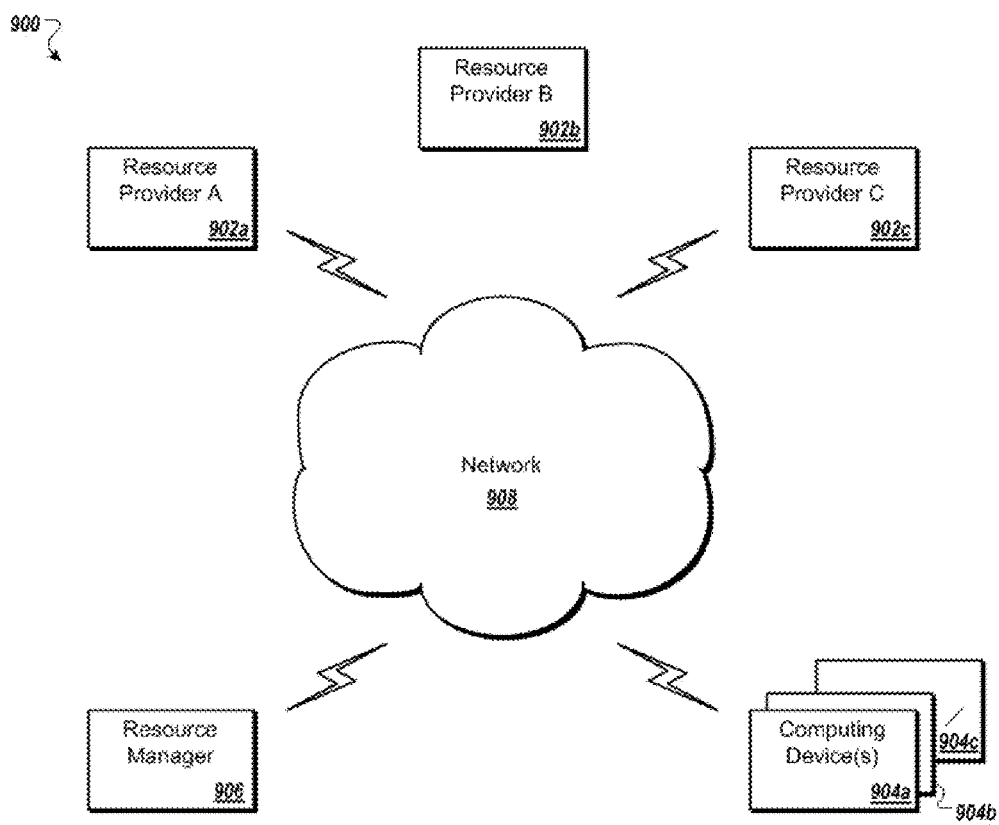
FIG. 9 is a block diagram of an example network environment for use in the methods and systems for analysis of micro-CT image data, according to an illustrative embodiment.

FIG. 9 shows an illustrative network environment 900 for use in the methods and systems for image segmentation and analysis, as described herein. In brief overview, referring now to FIG. 9, a block diagram of an exemplary cloud computing environment 900 is shown and described. The cloud computing environment 900 may include one or more resource providers 902a, 902b, 902c (collectively, 902). Each resource provider 902 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 902 may be connected to any other resource provider 902 in the cloud computing environment 900. In some implementations, the resource providers 902 may be connected over a computer network 908. Each resource provider 902 may be connected to one or more computing device 904a, 904b, 904c (collectively, 904), over the computer network 908.

The cloud computing environment 900 may include a resource manager 906. The resource manager 906 may be connected to the resource providers 902 and the computing devices 904 over the computer network 908. In some implementations, the resource manager 906 may facilitate the provision of computing resources by one or more resource providers 902 to one or more computing devices 904. The resource manager 906 may receive a request for a computing resource from a particular computing device 904. The resource manager 906 may identify one or more resource providers 902 capable of providing the computing resource requested by the computing device 904. The resource manager 906 may select a resource provider 902 to provide the computing resource. The resource manager 906 may facilitate a connection between the resource provider 902 and a particular computing device 904. In some implementations, the resource manager 906 may establish a connection between a particular resource provider 902 and a particular computing device 904. In some implementations, the resource manager 906 may redirect a particular computing device 904 to a particular resource provider 902 with the requested computing resource.

Figure 10:
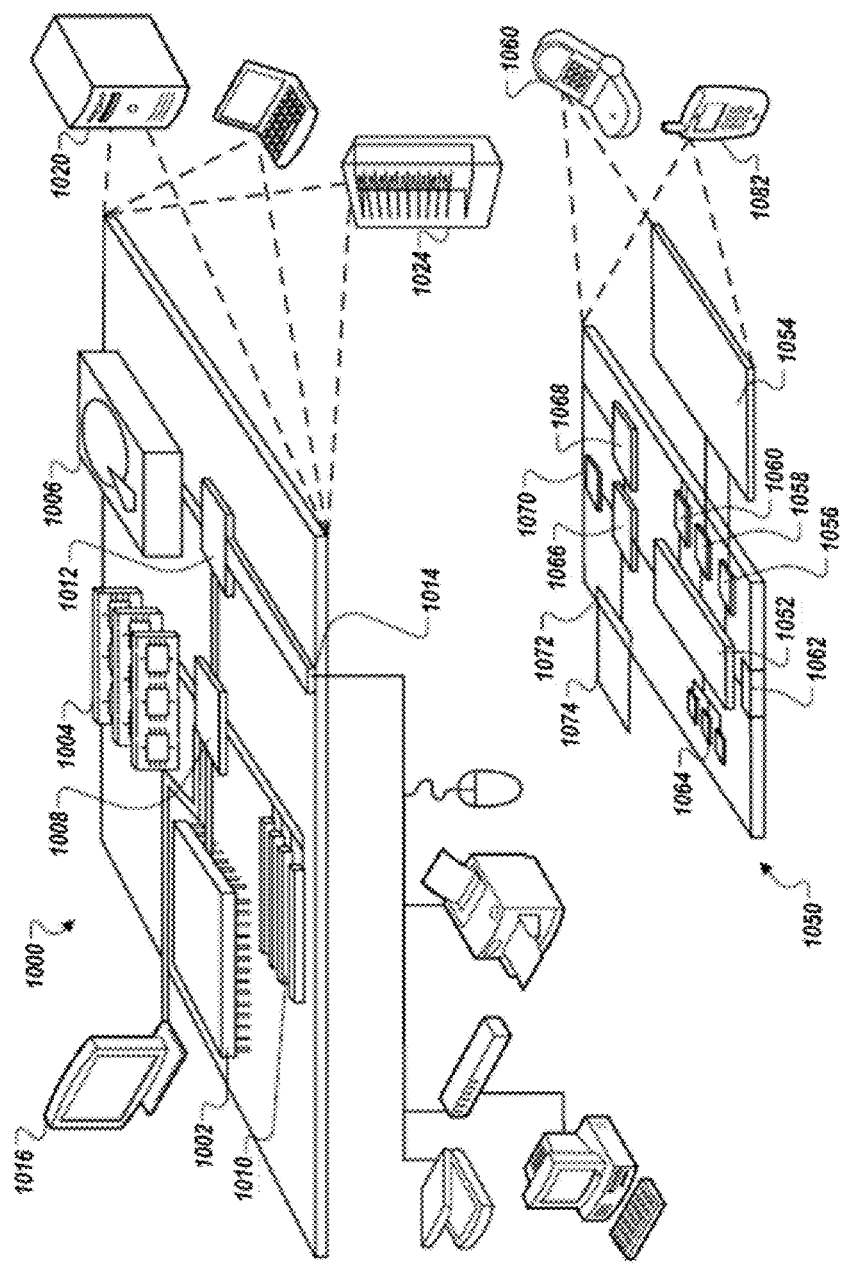
FIG. 10 is a block diagram of an example computing device and an example mobile computing device, for use in illustrative embodiments of the invention.

FIG. 10 shows an example of a computing device 1000 and a mobile computing device 1050 that can be used in the methods and systems described in this disclosure. The computing device 1000 is intended to represent various forms of digital computers, such as laptops, desktops, workstations, personal digital assistants, servers, blade servers, mainframes, and other appropriate computers. The mobile computing device 1050 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1000 includes a processor 1002, a memory 1004, a storage device 1006, a high-speed interface 1008 connecting to the memory 1004 and multiple high-speed expansion ports 1010, and a low-speed interface 1012 connecting to a low-speed expansion port 1014 and the storage device 1006. Each of the processor 1002, the memory 1004, the storage device 1006, the high-speed interface 1008, the high-speed expansion ports 1010, and the low-speed interface 1012, are interconnected using various busses, and may be mounted on a common motherboard or in other manners as appropriate. The processor 1002 can process instructions for execution within the computing device 1000, including instructions stored in the memory 1004 or on the storage device 1006 to display graphical information for a GUI on an external input/output device, such as a display 1016 coupled to the high-speed interface 1008. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 1004 stores information within the computing device 1000. In some implementations, the memory 1004 is a volatile memory unit or units. In some implementations, the memory 1004 is a non-volatile memory unit or units. The memory 1004 may also be another form of computer-readable medium, such as a magnetic or optical disk.

The storage device 1006 is capable of providing mass storage for the computing device 1000. In some implementations, the storage device 1006 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1002), perform one or more methods, such as those described above. The instructions can also be stored by one or more storage devices such as computer- or machine-readable mediums (for example, the memory 1004, the storage device 1006, or memory on the processor 1002).

The high-speed interface 1008 manages bandwidth-intensive operations for the computing device 1000, while the low-speed interface 1012 manages lower bandwidth-intensive operations. Such allocation of functions is an example only. In some implementations, the high-speed interface 1008 is coupled to the memory 1004, the display 1016 (e.g., through a graphics processor or accelerator), and to the high-speed expansion ports 1010, which may accept various expansion cards (not shown). In the implementation, the low-speed interface 1012 is coupled to the storage device 1006 and the low-speed expansion port 1014. The low-speed expansion port 1014, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1000 may be implemented in a number of different forms, as shown in the figure. For example, it may be implemented as a standard server 1020, or multiple times in a group of such servers. In addition, it may be implemented in a personal computer such as a laptop computer 1022. It may also be implemented as part of a rack server system 1024. Alternatively, components from the computing device 1000 may be combined with other components in a mobile device (not shown), such as a mobile computing device 1050. Each of such devices may contain one or more of the computing device 1000 and the mobile computing device 1050, and an entire system may be made up of multiple computing devices communicating with each other.

The mobile computing device 1050 includes a processor 1052, a memory 1064, an input/output device such as a display 1054, a communication interface 1066, and a transceiver 1068, among other components. The mobile computing device 1050 may also be provided with a storage device, such as a micro-drive or other device, to provide additional storage. Each of the processor 1052, the memory 1064, the display 1054, the communication interface 1066, and the transceiver 1068, are interconnected using various buses, and several of the components may be mounted on a common motherboard or in other manners as appropriate.

The processor 1052 can execute instructions within the mobile computing device 1050, including instructions stored in the memory 1064. The processor 1052 may be implemented as a chipset of chips that include separate and multiple analog and digital processors. The processor 1052 may provide, for example, for coordination of the other components of the mobile computing device 1050, such as control of user interfaces, applications run by the mobile computing device 1050, and wireless communication by the mobile computing device 1050.

The processor 1052 may communicate with a user through a control interface 1058 and a display interface 1056 coupled to the display 1054. The display 1054 may be, for example, a TFT (Thin-Film-Transistor Liquid Crystal Display) display or an OLED (Organic Light Emitting Diode) display, or other appropriate display technology. The display interface 1056 may comprise appropriate circuitry for driving the display 1054 to present graphical and other information to a user. The control interface 1058 may receive commands from a user and convert them for submission to the processor 1052. In addition, an external interface 1062 may provide communication with the processor 1052, so as to enable near area communication of the mobile computing device 1050 with other devices. The external interface 1062 may provide, for example, for wired communication in some implementations, or for wireless communication in other implementations, and multiple interfaces may also be used.

The memory 1064 stores information within the mobile computing device 1050. The memory 1064 can be implemented as one or more of a computer-readable medium or media, a volatile memory unit or units, or a non-volatile memory unit or units. An expansion memory 1074 may also be provided and connected to the mobile computing device 1050 through an expansion interface 1072, which may include, for example, a SIMM (Single In Line Memory Module) card interface. The expansion memory 1074 may provide extra storage space for the mobile computing device 1050, or may also store applications or other information for the mobile computing device 1050. Specifically, the expansion memory 1074 may include instructions to carry out or supplement the processes described above, and may include secure information also. Thus, for example, the expansion memory 1074 may be provided as a security module for the mobile computing device 1050, and may be programmed with instructions that permit secure use of the mobile computing device 1050. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 1052), perform one or more methods, such as those described above. The instructions can also be stored by one or more storage devices, such as one or more computer- or machine-readable mediums (for example, the memory 1064, the expansion memory 1074, or memory on the processor 1052). In some implementations, the instructions can be received in a propagated signal, for example, over the transceiver 1068 or the external interface 1062.

The mobile computing device 1050 may communicate wirelessly through the communication interface 1066, which may include digital signal processing circuitry where necessary. The communication interface 1066 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1068 using a radio-frequency. In addition, short-range communication may occur, such as using a Bluetooth®, Wi-Fi™, or other such transceiver (not shown). In addition, a GPS (Global Positioning System) receiver module 1070 may provide additional navigation- and location-related wireless data to the mobile computing device 1050, which may be used as appropriate by applications running on the mobile computing device 1050.

The mobile computing device 1050 may also communicate audibly using an audio codec 1060, which may receive spoken information from a user and convert it to usable digital information. The audio codec 1060 may likewise generate audible sound for a user, such as through a speaker, e.g., in a handset of the mobile computing device 1050. Such sound may include sound from voice telephone calls, may include recorded sound (e.g., voice messages, music files, etc.) and may also include sound generated by applications operating on the mobile computing device 1050.

The mobile computing device 1050 may be implemented in a number of different forms, as shown in the figure. For example, it may be implemented as a cellular telephone 1080. It may also be implemented as part of a smart-phone 1082, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

What is claimed is:

1. A method of performing image segmentation to automatically differentiate individual bones in an image of a skeleton or partial skeleton of a subject, the method comprising:
   receiving, by a processor of a computing device, a three-dimensional image of a subject;
   applying, by the processor, one or more second derivative splitting filters to the image to produce a split bone mask for the image with bone boundaries removed;
   determining, by the processor, a plurality of split binary components of the split bone mask by performing one or more morphological processing operations; and
   performing, by the processor, a region growing operation using the split binary components of the split bone mask as seeds, thereby producing a segmentation map differentiating individual bones in the image.

2. The method of claim 1, wherein the one or more second derivative splitting filters comprises at least one member selected from the group consisting of a LoG (Laplacian of Gaussian), a HEH (highest Hessian eigenvalue, with preliminary Gaussian filtering), and a LEH (lowest Hessian eigenvalue, with preliminary Gaussian filtering).

3. The method of claim 1, comprising applying a plurality of second derivative splitting filters to the image of the subject to produce the split bone mask, the applying step comprising:
   for each second derivative splitting filter being applied, producing a filtered image and identifying voxels of the filtered image with intensity higher or lower than a threshold, thereby yielding a split binary mask identifying voxels in the vicinity of a boundary region between adjacent bones;
   combining the split binary masks by performing one or more logical operations to return the split bone mask (which is a hybrid of the split binary masks), with voxels near bone boundaries removed.

4. The method of claim 1, further comprising identifying, by the processor, one or more anatomical measurements, using the segmentation map.

5. The method of claim 1, further comprising, following the step of producing the segmentation map, accepting feedback from a user identifying one or more segmented regions of the segmentation map for further refinement or recalculation and then:
   applying, by the processor, one or more second derivative splitting filters to portions of the image corresponding to the one or more user-identified segmented regions to produce a split bone mask;
   determining, by the processor, split binary components of the split bone mask; and
   performing, by the processor, a region growing operation using the split bone mask components as seeds, thereby producing a refined or recalculated segmentation map differentiating individual bones in the image.

6. The method of claim 1, wherein the image of the subject has a resolution such that each voxel of the image corresponds to a volume at least 40 microns in each dimension.

7. The method of claim 1, wherein at least one of the one or more second derivative splitting filters is applied using one or more rotational invariants of spatial second partial derivatives of the voxel intensities of the image, wherein the image is a three-dimensional gray-scale image.

8. The method of claim 1, wherein the image is an in vivo image.

9. The method of claim 1, wherein the subject is a small mammal subject.

10. The method of claim 1, wherein the image is obtained by a micro-CT imager.

11. The method of claim 1, wherein determining the plurality of split binary components of the split bone mask is carried out by performing connected component analysis and/or by identifying catchment basins using distance and watershed transforms.

12. The method of claim 1, comprising quantifying, by the processor, a volume of each split binary component of the split bone mask and eliminating, by the processor, one or more split binary components of the split binary bone mask having unacceptably small volume.

13. A system comprising:
   a processor; and
   a memory having instructions stored thereon, wherein the instructions, when executed by the processor, cause the processor to:
   receive a three-dimensional image of a subject;
   apply one or more second derivative splitting filters to the image to produce a split bone mask for the image with bone boundaries removed;
   determine a plurality of split binary components of the split bone mask by performing one or more morphological processing operations; and
   perform a region growing operation using the split binary components of the split bone mask as seeds, thereby producing a segmentation map differentiating individual bones in the image.

14. The system of claim 13, wherein the one or more second derivative splitting filters comprises at least one member selected from the group consisting of a LoG (Laplacian of Gaussian), a HEH (highest Hessian eigenvalue, with preliminary Gaussian filtering), and a LEH (lowest Hessian eigenvalue, with preliminary Gaussian filtering).

15. The system of claim 13, wherein the instructions, when executed by the processor, further cause the processor to apply a plurality of second derivative splitting filters to the image of the subject to produce the split bone mask, the applying step comprising:

for each second derivative splitting filter being applied, producing a filtered image and identifying voxels of the filtered image with intensity higher or lower than a threshold, thereby yielding a split binary mask identifying voxels in the vicinity of a boundary region between adjacent bones;

combining the split binary masks by performing one or more logical operations to return the split bone mask (which is a hybrid of the split binary masks), with voxels near bone boundaries removed.

16. The system of claim 13, wherein the instructions, when executed by the processor, further cause the processor to identify one or more anatomical measurements using the segmentation map.

17. The system of claim 13, wherein the instructions, when executed by the processor, further cause the processor to, following the step of producing the segmentation map, accept feedback from a user identifying one or more segmented regions of the segmentation map for further refinement or recalculation and then:

apply one or more second derivative splitting filters to portions of the image corresponding to the one or more user-identified segmented regions to produce a split bone mask;

determine split binary components of the split bone mask; and perform a region growing operation using the split bone mask components as seeds, thereby producing a refined or recalculated segmentation map differentiating individual bones in the image.

18. The system of claim 13, wherein the image of the subject has a resolution such that each voxel of the image corresponds to a volume at least 40 microns in each dimension.

19. The system of claim 13, wherein at least one of the one or more second derivative splitting filters is applied using one or more rotational invariants of spatial second partial derivatives of the voxel intensities of the image, wherein the image is a three-dimensional gray-scale image.

20. The system of claim 13, wherein the image is an in vivo image.

21. The system of claim 13, wherein the subject is a small mammal subject.

22. The system of claim 13, wherein the image is obtained by a micro-CT imager.

23. The system of claim 13, wherein determining the plurality of split binary components of the split bone mask is carried out by performing connected component analysis and/or by identifying catchment basins using distance and watershed transforms.

24. The system of claim 13, wherein the instructions cause the processor to quantify a volume of each split binary component of the split bone mask and eliminate one or more components having unacceptably small volume.

25. A non-transitory computer readable medium having instructions stored thereon, wherein the instructions, when executed by a processor, cause the processor to:

receive a three-dimensional image of a subject;

apply one or more second derivative splitting filters to the image to produce a split bone mask for the image with bone boundaries removed;

determine a plurality of split binary components of the split bone mask by performing one or more morphological processing operations; and perform a region growing operation using the split binary components of the split bone mask as seeds, thereby producing a segmentation map differentiating individual bones in the image.

26. The non-transitory computer readable medium of claim 25, wherein the instructions cause the processor to quantify a volume of each split binary component of the split bone mask and eliminate one or more components having unacceptably small volume.

* * * * *